United States Patent [19]

Dagger

[11] Patent Number: 5,719,293
[45] Date of Patent: Feb. 17, 1998

[54] INTERMEDIATE FOR PREPARING A PHARMACEUTICALLY ACTIVE COMPOUND

[75] Inventor: Raymond E. Dagger, Warminster, Pa.

[73] Assignee: SmithKline Beecham Corporation, Philadelphia, Pa.

[21] Appl. No.: 737,699

[22] PCT Filed: May 4, 1995

[86] PCT No.: PCT/US95/05664

§ 371 Date: Nov. 20, 1996

§ 102(e) Date: Nov. 20, 1996

[87] PCT Pub. No.: WO95/32189

PCT Pub. Date: Nov. 30, 1995

[51] Int. Cl.⁶ .................................................. C07D 233/64
[52] U.S. Cl. .................................. 548/341.5; 548/342.1
[58] Field of Search ........................... 548/341.5, 342.1

[56] References Cited

U.S. PATENT DOCUMENTS 4,355,040 10/1982 Furukawa et al. ................... 424/273 R
5,185,351 2/1993 Finkelstein et al. ..................... 514/341
5,254,546 10/1993 Ardecky et al. ....................... 514/225.8

OTHER PUBLICATIONS

J. Marc, "Advanced Organic Chemistry" published 1992 by John Wiley & sons (N.Y.), see p. 895, section 6–12.

*Primary Examiner*—Floyd D. Higel
*Attorney, Agent, or Firm*—Mary E. McCarthy; Stephen A. Venetianer; Edward T. Lentz

[57] ABSTRACT

This invention relates to a compound of formula (I) and hydrates, solvates, and salts thereof.

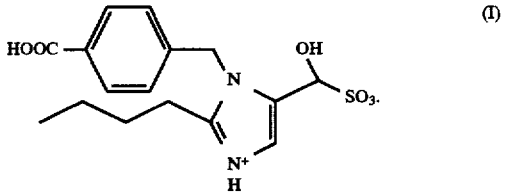

2 Claims, No Drawings

INTERMEDIATE FOR PREPARING A PHARMACEUTICALLY ACTIVE COMPOUND

This application is a 371 of PCT/U.S. application Ser. No. 95/05664 filed May 4, 1995.

FIELD OF THE INVENTION

The present invention relates to the bisulfite addition compound of a key intermediate useful in the preparation of an angiotensin II (AII) receptor antagonist.

BACKGROUND OF THE INVENTION

PCT Application WO 94/06776 published Mar. 31, 1994 describes a process for preparing 1-alkylaryl-2-alkyl-5-formylimidazoles which comprises reacting a 2-halo-2-propenal-3-alkyl ether, such as 2-bromo-3-(1-methylethoxy)-2-propenal, with a N-(1-iminoalkyl)aminoalkylaryl compound, such as N-(1-iminopentyl)-4-(aminomethyl) benzoic acid. In particular, the PCT application details the preparation of 4-[(2-n-butyl-5-formyl-1H-imidazol-1-yl) methyl]benzoic acid, which is a key intermediate in the preparation of (E)-3-[2-n-butyl-1-{(4-carboxyphenyl) methyl-1H-imidazol-5-yl]-2-(2-thienyl)methyl-2-propenoic acid, a highly potent AII receptor antagonist (Weinstock, et al., *J. Med. Chem.*, 34:1514–1517 (1991)). Although the process described in PCT Application WO 94/06776 produces the key intermediate in high yield and high purity, the isolation of said intermediate involves a lengthy procedure consisting of multiple extractions, a slurry with montmorillonite K-10 clay, and a distillation/crystallization sequence. Thus, there is a need for an alternate method for the isolation of 4-[(2-n-butyl-5-formyl-1H-imidazol-1-yl)methyl] benzoic acid, particularly when preparing this intermediate on a commercial scale for use in the synthesis of (E)-3-[2-n-butyl-1-{(4-carboxyphenyl)methyl-1H-imidazol-5-yl]-2-(2-thienyl)methyl-2-propenoic acid.

It has now been found that purified 4-[(2-n-butyl-5-formyl-1H-imidazol-1-yl)methyl]benzoic acid can be obtained by converting the intermediate to its bisulfite addition compound, recrystallizing the addition compound and then reconverting said addition compound to 4-[(2-n-butyl-5-formyl-1H-imidazol-1-yl)methyl]benzoic acid. Also, the bisulfite addition compound itself can be used directly in the preparation of ethyl (E) -3-[2-n-butyl-1 -{(4-carboxyphenyl)methyl-1H-imidazol-5-yl]-2-(2-thienyl) methyl-2-propenoate, which is the immediate precussor to (E)-3-[2-n-butyl-1-{(4-carboxyphenyl)methyl-1H-imidazol-5-yl]-2-(2-thienyl)methyl-2-propenoic acid. The ease of work-up and the efficiency of the isolation process which makes use of the bisulfite addition compound of 4-[(2-n-butyl-5-formyl-1H-imidazol-1-yl)methyl]benzoic acid is advantageous from a commercial viewpoint.

SUMMARY OF THE INVENTION

The present invention provides for a compound according to the formula (I):

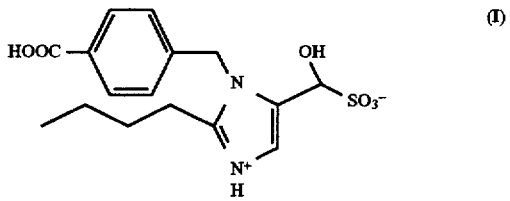

and hydrates, solvates, and salts thereof.

DETAILED DESCRIPTION OF THE INVENTION

This invention relates to a compound of the formula (I):

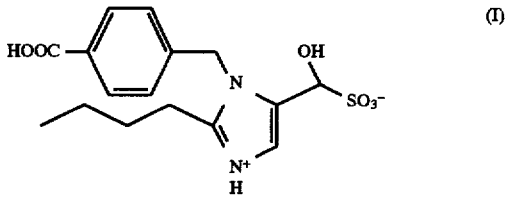

and hydrates, solvates, and salts thereof.

The specific compound of this invention is the bisulfite addition compound of 4-[(2-n-butyl-5-formyl-1H-imidazol-1-yl)methyl]benzoic acid, and hydrates, solvates, and salts thereof.

Generally, the compound of formula (I) is prepared by reacting a compound of formula (II):

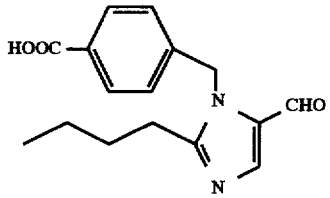

with sodium bisulfite.

Specifically, the compound of the formula (I) is prepared by the method described in Scheme I.

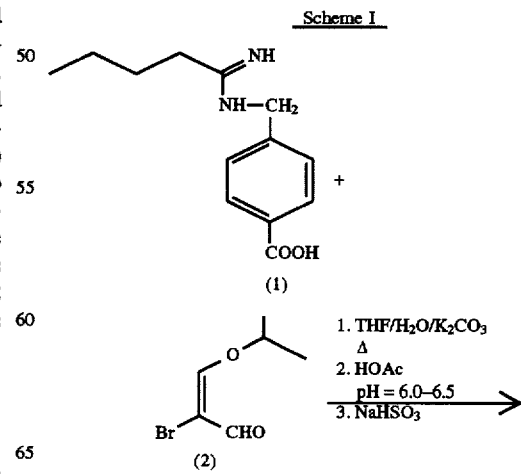

-continued
Scheme I

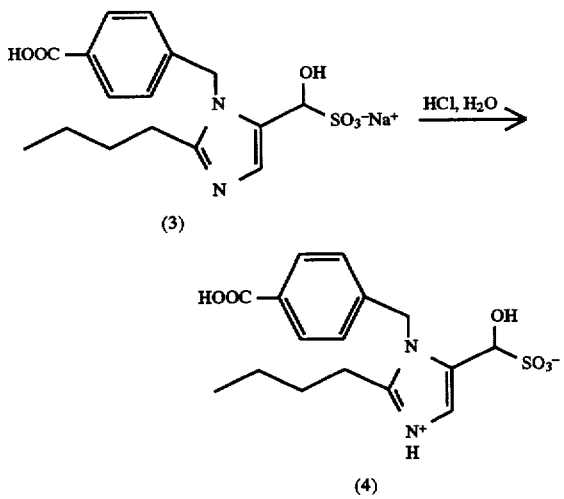

According to Scheme I, 4-[(2-n-butyl-5-formyl-1H-imidazol-1-yl)methyl]benzoic acid is formed by reacting N-(1-iminopentyl)-4-(aminomethyl)benzoic acid (formula (I) compound in Scheme I) with 2-bromo-3-(1-methylethoxy)-2-propenal (formula (2) compound in Scheme I) in the presence of a base, for example, potassium carbonate. (See PCT Application WO 94/06776.) The resulting 5-formyl imidazole compound (formula (II) compound), without isolation, is then reacted with sodium bisulfite to yield the intermediate sodium salt of the bisulfite addition compound (formula (3) in Scheme I). Treatment of the formula (3) compound with aqueous hydrochloric acid (pH 1.0–1.5) resulted in the formation of the formula (4), Scheme I, compound, which is also a formula (I) compound. 4-[(2-n-Butyl-5-formyl-1H-imidazol-1-yl)methyl]benzoic acid may then be regenerated by reacting the formula (4) Scheme (I) compound with a mixture of water, acetic acid and hydrochloric acid under nitrogen.

The compound of formula (I) may exist in hydrated or solvated form. Any and all such hydrates and solvates are included within the scope of this invention.

Salts of the compound of formula (I), such as the formula (3) Scheme (I) compound, may be prepared by known methods from inorganic bases, including alkali metal and alkaline earth bases, for example, lithium, sodium and potassium hydroxides, bicarbonates, and carbonates, and organic bases, such as triethylamine, butylamine, piperazine, choline and diethanolamine.

Use of the compound of this invention provides a new method for isolating and purifying a key intermediate in the synthesis of a potent angiotensin II receptor antagonist. This isolation/purification process via the formation of the bisulfite addition compound of 4-[(2-n-butyl-5-formyl-1H-imidazol-1-yl)methyl]benzoic acid allows for the production of the key intermediate in a simplified manner, which is particularly useful when preparing this intermediate on a commercial scale.

The invention is illustrated by the following example. The example is not intended to limit the scope of this invention as defined hereinabove and as claimed hereinbelow.

EXAMPLE 1

Synthesis of the bisulfite addition compound of 4-[(2-butyl-5-formyl-1H-imidazol-1-yl)methyl]benzoic acid N-(1-iminopentyl)-4-(aminomethyl)benzoic acid (80 mMol, 19.13 g @80%), 2-bromo-3-(1-methylethoxy)-2-propenal (88 mMol, 18.9 g @90%), potassium carbonate (104 mMol, 14,42 g), tetrahydrofuran (90 mL) and water (10 mL) are combined, stirred vigorously and refluxed under a nitrogen atmosphere. After 3 hours of reflux, additional amounts of 2-bromo-3-(1-methylethoxy)-2-propenal (12 mMol, 2.6 g @90%) and potassium carbonate (15 mMol, 2.1 g) are added. After 4.5 hours of reflux, additional mounts of 2-bromo-3-(1-methylethoxy)-2-propenal (6.0 mMol, 1.3 g @90%) and potassium carbonate (7.5 mMol, 1.05 g) are added. After 6–7 hours of reflux, the reaction is cooled to ambient temperature. The mixture is diluted with water (25 mL) and the pH is adjusted to 6.0–6.5 with glacial acetic acid (as needed). The neutralized reaction is diluted with tert-butylmethyl ether (90 mL). Sodium bisulfite (20 g) and sodium chloride (16 g) are added to the well stirred mixture. The mixture is cooled to 0°–5° C., stirred for 2 hours and the intermediate sodium salt of the bisulfite addition compound (formula (3) compound in Scheme I) is isolated via vacuum filtration. This intermediate salt is dissolved in water (275 mL) and the resultant solution is acidified to pH 1.0–1.5 with hydrochloric acid. The resultant mixture is cooled to 3°–7° C. for 2–3 hours and the desired bisulfite addition compound (formula (4) compound in Scheme I) is isolated via vacuum filtration as a white, water-wet solid in 70% crude yield. Recrystallization of this wet solid from glacial acetic acid (40 mL) at 90° C. produces the title compound as a white solid in 60% (29.5 g) yield after drying in vacuo.

IR(FT, KBr): 3600–3100, N—H and O—H (hydroxyl) stretch; 3300–2800, O—H (acid) stretch; 3100–2800, —C—H and =C—H stretches; 2800–2400, NH$^+$stretch; 1708, C=O (carboxylic acid) stretch; 1614, C=N and C=C stretches; 1250–1160, C—O and O—H (hydroxyl) stretch, C—O (acid) stretch, and SO$_2$ stretch; 1040 and 1014, C—O and O—H (hydroxyl) stretch and SO$_3$— vibration (cm$^{-1}$).

It is to be understood that the invention is not limited to the embodiment illustrated hereinabove and the fight to the illustrated embodiment and all modifications coming within the scope of the following claim is reserved.

What is claimed is:

1. A compound of the formula (I):

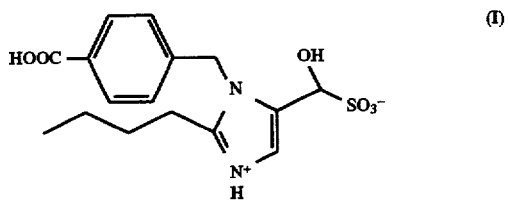

or a hydrate, solvate, or salt thereof.

2. A process for preparing a compound of the formula (I) or a hydrate, solvate, or salt thereof, as defined in claim 1, which process comprises reacting a compound of the formula (II):

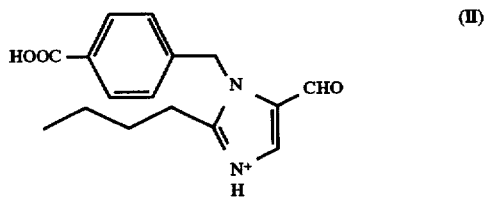

with sodium bisulfite.

* * * * *